US012533014B2

(12) United States Patent

Long et al.

(10) Patent No.: US 12,533,014 B2
(45) Date of Patent: Jan. 27, 2026

(54) DISPOSABLE INTRODUCER FOR ADVANCING AN ELONGATE MEMBER INTO A TUBULAR STRUCTURE

(71) Applicant: Light Line Medical, Inc., Salt Lake City, UT (US)

(72) Inventors: Curtis D. Long, Salt Lake City, UT (US); Robert W Hitchcock, Salt Lake City, UT (US); John Lackey, West Valley City, UT (US)

(73) Assignee: Light Line Medical, Inc., Salt Lake City, UT (US)

( * ) Notice: Subject to any disclaimer, the term of this patent is extended or adjusted under 35 U.S.C. 154(b) by 432 days.

(21) Appl. No.: 17/985,885

(22) Filed: Nov. 13, 2022

(65) Prior Publication Data

US 2024/0156333 A1 May 16, 2024

(51) Int. Cl.

*A61B 1/00* (2006.01)
*A61M 25/00* (2006.01)
*A61M 39/10* (2006.01)

(52) U.S. Cl.

CPC ......... *A61B 1/00154* (2013.01); *A61M 25/00* (2013.01); *A61M 39/10* (2013.01)

(58) Field of Classification Search

CPC .... A61B 1/00154; A61B 1/018; A61M 25/00; A61M 39/10; A61M 25/09041; A61M 2025/0019; A61M 25/0097

See application file for complete search history.

(56) References Cited

U.S. PATENT DOCUMENTS 4,412,834 A 11/1983 Kulin et al.
4,512,762 A 4/1985 Spears
4,793,350 A * 12/1988 Mar .................. A61M 25/0133 604/103.1

(Continued)

FOREIGN PATENT DOCUMENTS

WO WO2006/074509 7/2006
WO WO-2006074509 A1 * 7/2006 ......... A61B 17/3403
WO WO2019/027478 2/2019

OTHER PUBLICATIONS

Examination of SMA Connector Parameters (Year: 2012).*

*Primary Examiner* — Anh Tuan T Nguyen
*Assistant Examiner* — Shankar Raj Ghimire
(74) *Attorney, Agent, or Firm* — Madson IP, P.C.

(57) ABSTRACT

An introducer assembly introduces an elongate member into a tubular structure and may be configured into ready, introduced, and detached modes. The introducer assembly has a guide tube, a slide collar, and proximal and distal connector assemblies. The guide tube has a proximal body, and a distal portion, the distal portion being rotatably connected to the proximal body. The slide collar has a grip, a slide post, and a centered capture structure. The proximal connector assembly is detachably nested within the centered capture structure. The distal connector assembly is detachably nested within the distal portion and is connectable to the tubular structure. The introducer assembly may be converted from the ready mode to the introduced mode to the detached mode by manual manipulation to introduce and secure the elongate member within the connected tubular structure, and then detach the guide tube leaving the elongate member within the connected tubular structure.

20 Claims, 11 Drawing Sheets

(56) References Cited

U.S. PATENT DOCUMENTS 5,053,003 A 10/1991 Dadson et al.
5,260,020 A 11/1993 Wilk et al.
5,445,608 A 8/1995 Chen et al.
5,607,419 A 3/1997 Amplatz et al.
5,637,877 A 6/1997 Sinofsky
5,695,482 A 12/1997 Kaidany
5,702,432 A 12/1997 Chen et al.
5,855,203 A 1/1999 Matter
6,119,037 A 9/2000 Kellogg et al.
6,183,450 B1 * 2/2001 Lois ...................... A61M 25/00 604/164.01
6,273,895 B1 * 8/2001 Pinchuk .................... A61F 2/95 623/1.11
6,461,569 B1 10/2002 Boudreaux
6,551,346 B2 4/2003 Crossley
6,562,295 B1 5/2003 Neuberger
7,232,429 B2 6/2007 Moreci
7,356,225 B2 4/2008 Loebel
7,449,026 B2 11/2008 Zalesky
7,730,894 B2 6/2010 Bishop et al.
7,950,396 B2 5/2011 Rose et al.
8,057,464 B2 11/2011 Chen et al.
8,247,406 B2 8/2012 Street et al.
8,377,012 B2 * 2/2013 Chapman .............. A61M 39/28 604/523
8,618,091 B2 12/2013 Street et al.
8,636,706 B2 1/2014 Chapman et al.
8,933,416 B2 1/2015 Arcand et al.
9,039,966 B2 5/2015 Anderson et al.
10,894,173 B2 1/2021 Barneck et al.
11,241,585 B2 2/2022 Long et al.
2003/0018324 A1 1/2003 Davenport et al.
2004/0039242 A1 2/2004 Tolkoff et al.
2004/0193218 A1 9/2004 Butler
2005/0090722 A1 4/2005 Perez
2006/0009821 A1 1/2006 Perez
2007/0027443 A1 2/2007 Rose et al.
2007/0197860 A1 * 8/2007 Ishizaki ............... A61B 1/0055 600/101
2007/0219605 A1 9/2007 Yaroslavsky et al.
2007/0255356 A1 11/2007 Rose et al.
2007/0255357 A1 11/2007 Rose et al.
2007/0260231 A1 11/2007 Rose et al.
2007/0260295 A1 11/2007 Chen et al.
2008/0051736 A1 2/2008 Rioux et al.
2008/0154317 A1 6/2008 Loebel
2008/0159908 A1 7/2008 Redmond
2008/0255549 A1 10/2008 Rose et al.
2008/0269845 A1 10/2008 Rose et al.
2008/0306454 A1 12/2008 Sikora
2009/0048648 A1 2/2009 Dacey, Jr. et al.
2009/0093470 A1 4/2009 Loebel et al.
2009/0257910 A1 10/2009 Segal
2010/0072399 A1 3/2010 Street et al.
2010/0246169 A1 9/2010 Anderson et al.
2010/0256607 A1 10/2010 Burnett
2011/0085936 A1 4/2011 Deutsch et al.
2011/0208274 A1 8/2011 Bornstein
2011/0295343 A1 12/2011 Bornstein et al.
2012/0321509 A1 12/2012 Bak
2013/0030249 A1 * 1/2013 Vazales ............. A61M 16/0427 600/120
2013/0060188 A1 3/2013 Bedwell et al.
2013/0267888 A1 10/2013 Rhodes et al.
2013/0303996 A1 11/2013 Rasooly et al.
2014/0058253 A1 2/2014 Prough et al.
2014/0150782 A1 6/2014 Vazales et al.
2014/0235942 A1 8/2014 Hellstrom et al.
2015/0057648 A1 2/2015 Swift et al.
2015/0231287 A1 * 8/2015 Lin ................... A61M 25/0097 607/80
2015/0297767 A1 10/2015 Gaska et al.
2015/0343182 A1 * 12/2015 Vazales ............. A61M 16/0463 604/267
2016/0151639 A1 6/2016 Scharf et al.
2016/0256646 A1 * 9/2016 Vazales ............... A61M 13/003
2016/0279402 A1 9/2016 Stigall et al.
2016/0317832 A1 11/2016 Barneck et al.
2017/0042571 A1 * 2/2017 Levi ................... A61M 25/0113
2017/0259043 A1 * 9/2017 Chan ..................... A61M 29/02
2018/0015302 A1 * 1/2018 Barneck ............... A61N 5/0624
2018/0178029 A1 * 6/2018 Rogers ................... A61B 18/24
2018/0200496 A1 * 7/2018 Kratzberg ............... A61F 2/966
2019/0217117 A1 * 7/2019 Barneck ............ A61M 25/0028
2019/0321590 A1 * 10/2019 Burkholz ................ A61M 5/14
2019/0358387 A1 11/2019 Elbadry et al.
2020/0121359 A1 * 4/2020 Rokde ................ A61B 1/00167
2021/0299426 A1 * 9/2021 Scherich ............... A61M 5/158
2022/0079625 A1 * 3/2022 Einarsson ............ A61B 90/361
2022/0079696 A1 * 3/2022 Nichols ..................... A61B 1/04
2022/0296263 A1 * 9/2022 Hirata .................. A61B 1/0014
2023/0045573 A1 * 2/2023 Nelson .................. A61M 39/04
2023/0309878 A1 * 10/2023 Burkholz ........... A61M 25/0113

* cited by examiner

DISPOSABLE INTRODUCER FOR ADVANCING AN ELONGATE MEMBER INTO A TUBULAR STRUCTURE

RELATED APPLICATIONS

This application relates to, but does not claim priority to, U.S. patent application Ser. No. 17/579,657, filed Jan. 20, 2022, and titled ELECTROMAGNETIC RADIATION DELIVERY AND MONITORING SYSTEM AND METHODS FOR PREVENTING, REDUCING AND/OR ELIMINATING CATHETER-RELATED INFECTIONS DURING INSTITUTIONAL OR IN-HOME USE and published as U.S. Publication No. 2022/0257975 ("Pending Application"). This application is also being filed concurrently with a continuation-in-part of the Pending application, U.S. patent application (application No. presently unknown) filed Nov. 13, 2022, and titled A DISPOSABLE FIBER OPTIC INTRODUCER COMPONENT OF A LIGHT DELIVERY SYSTEM FOR PREVENTING, REDUCING, AND/OR ELIMINATING INFECTIONS DURING INSTITUTIONAL OR IN-HOME USE. Each of the related applications referred to in this paragraph is hereby incorporated by this reference as if fully set forth herein.

TECHNICAL FIELD

The present invention is an apparatus and system to introduce an elongate member into a tubular-receiving structure. The present invention is particularly suitable in introducing a fiber optic into a tubular structure such as a 3-port adaptor, an extension set, and/or a catheter, individually or in combination, to provide versatile delivery and monitoring of therapeutic doses of non-ultraviolet light to inactivate infectious agents residing on, within, or generally around a catheter while the catheter is residing within a body cavity or residing on, within, or around extension sets and connectors outside the body along the flow path of fluids such as dialysate and waste dialysate, blood, urine, medicating fluids, and the like, and to stimulate healthy cell growth within the body and at the entry/exit site causing a healing effect.

Frequently, extension sets are also called catheter extensions, catheter extension sets, and transfer sets. For the purposes of this disclosure, the terms "extension set" or "extension sets" shall be considered generic terms having meaning that includes catheter extensions, catheter extension sets, transfer sets, and any other commonly used term for these types of structures.

Various types of medical introducers are known and have been used for years in the institutional setting by highly trained doctors, nurses, and clinicians. However, as more medical treatments and procedures are being performed by caregivers having limited or no medical training and patients themselves at home, the intricate institutional introducers that require delicate handling and stringent handling procedures to maintain sterilization are not suitable for in-home use. The apparatus and system disclosed herein is designed to be inexpensive, as well as, ergonomic and intuitive for caregivers and patients while minimizing infection risk but may be suitable for various institutional uses where high-priced, intricate introducers are not required. For example, the apparatus and system disclosed herein may be used for non-medical uses and medical uses (institutional or in-home) to introduce elongate members into tubular-receiving structures.

Because the apparatus and system disclosed herein may be utilized in various embodiments for a broad range of uses, medical and non-medical, exemplary uses will be disclosed herein and described such that an artisan having ordinary skill in the art related to the disclosed use, armed with the entirety of the disclosure herein, will be able to make and use the apparatus and system for such exemplary uses. However, in the interest of a more succinct disclosure not all embodiments contemplated herein are depicted in drawings or described in detail.

This disclosure is of an introducer assembly that is particularly suitable for use with a fiber optic to deliver non-ultraviolet visual therapeutic electromagnetic radiation (EMR) at a high enough intensity to stimulate healthy cell growth causing a healing effect and/or to reduce or eliminate infectious agents in, on, and around a catheter while the catheter resides inside a body cavity and/or in, on, and around the extension sets and/or connectors outside the body along the flow path of fluids such as dialysate and waste dialysate.

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "some embodiments," "various embodiments," and the like, may indicate that the embodiment(s) of the invention so described may include a particular feature, structure, or characteristic, but not every embodiment necessarily includes a particular feature, structure, or characteristic. Further, repeated use of the phrase "in one embodiment," or "in an exemplary embodiment," do not necessarily refer to the same embodiment, although they may.

BACKGROUND

Catheters are tubular structures commonly used as channels to inject medications into or retrieve fluid samples from a patient. Each catheter comprises a tube, usually derived from plastic or other polymers, such as silicone, polyurethane, and the like, that at least a portion thereof may be inserted into an area of the body and may contain one or more separate lines in which these fluids may be delivered or retrieved. A "lumen" designates a pathway in the catheter that goes from outside the body to inside the body. Catheters and other tubular structures are used in various applications, including intravascularly, abdominally, urologically, gastrointestinally, ophthalmically, within the respiratory tract, within cranial space, within the spinal column, during dialysis and the like. In all cases, the catheter extends from outside the body to be placed inside of a space in the body where the catheter or a portion of a catheter assembly resides, herein referred to as a "body cavity". These devices frequently give rise to infections caused by growth of infectious agents in, on, and around the catheter and on tissue surrounding the catheter. Infectious agents can include bacteria, fungi, viruses, or the like that enter the body and lead to illness in a patient. Depending on the location of the catheter placement, these infections can arise in the form of urinary tract infections, blood stream infections, soft tissue infection, and the like.

Catheter related infections (CRIs) are a large problem in medicine, leading to high morbidity and mortality rates. Current methods of reducing or eliminating the number of infectious agents in, on, or around a catheter are of low efficacy. Typically, catheters will be removed if they are suspected to be harboring infectious agents, increasing both the cost associated with treatment and patient discomfort. Various methods to deter or eliminate growth of infectious agents in, on, and around catheters have been attempted, such as using sterile handling techniques, antibiotics, and replacing the catheter when an infection is suspected. Despite these techniques, infections resulting from catheters remain a major problem. These infections, along with urinary tract infections, gastrointestinal infections, dialysis-related infections, and other infections from catheters and extension sets, increase medical costs, insurance costs, and patient discomfort.

The emergence of infectious agents that are resistant to current treatments, such as methicillin-resistance *Staphylococcus aureus* (MRSA), further substantiates the need for another treatment of CRIs. To reduce the costs associated with removing and replacing the catheters from and into the patient, there is a need for sterilization of the entire catheter and/or catheter-related assemblies while at least a portion of the catheter resides in the patient. Additionally, it would be advantageous to be able to stimulate healthy cell growth by providing therapeutic EMR via such indwelling catheters.

Heretofore, however, there has never been apparatus or methods for making or using such apparatus to disinfect a catheter safely and effectively while it is indwelling within a patient. Accordingly, there exists a need for methods and apparatus designed to deliver non-antibiotic, bactericidal therapeutics in-vivo. Such methods and apparatus, using novel technology, may provide removable delivery of safe, effective, and reproducible disinfection and/or enhance healthy cell growth.

Additionally, with the rising costs of health care in hospitals and clinics, recently more emphasis and motivation for developing in-home treatments has led to advances that provide significant cost savings and patient comfort and improved lifestyle. However, developing in-home treatments have ushered in a dangerous escalation in infections and the costs associated with dealing with such infections. The apparatus and system disclosed herein is designed to be inexpensive, as well as ergonomic and intuitive for caregivers and patients while minimizing or even eliminating infection risks.

SUMMARY OF THE INVENTION

The exemplary embodiments of this disclosure relate to medical device assemblies for introducing and inserting elongate members such as, for example, a guide wire, an endoscope, an angioscope, a hysteroscope, a gastroscope, a flexible telescope for colonoscopies, bronchoscope, a cystoscope, probes for illumination, probes for pinpoint medication or treatment delivery, probes for inflation gas delivery, fiber optics, and any of numerous other devices or instruments that are elongate and may be inserted into and/or retracted from a cavity of a patient's body and/or from within tubular structures outside a patients body. Frequently, catheters and other tubular structures facilitate delivery of fluids from outside the body to inside the body and retrieval of fluids from inside the body to outside the body, and reducing, inhibiting, preventing, or eliminating infectious agents before, during, or after delivery and/or retrieval of fluids may be of paramount concern. Hence, an introducing assembly or system that enables the appropriate elongate member to be introduced into catheters or other tubular structures, without compromising sterility or unduly inhibiting fluid flow, would advance in-home as well as institutional treatments.

Some exemplary embodiments of this disclosure are directed to an introducer assembly for introducing an elongate member into a tubular-receiving structure, where the introducer assembly has a ready mode, an introduced mode, and a detached mode. The ready mode being a configuration of the introducer assembly during shipping and/or storage typically wherein the introducer assembly is maintained sterile and elongate member is housed and secured within a protective guide tube. The introduced mode being a configuration of the introducer assembly after being connected to the tubular-receiving structure and the elongate member is advanced into the tubular-receiving structure to reside therein after securing the elongate member in place. Once the elongate member is secured in place, the guide tube of the introducer assembly may be detached from the elongate member for disposal, thereby changing the introducer assembly from the introduced mode to detached mode.

An exemplary embodiment of the introducer assembly has a guide tube, a slide collar, a proximal connector assembly, and a distal connector assembly. The guide tube has a longitudinal axis, a proximal body, and a distal portion. The distal portion may be connected rotatably to the proximal body such that the distal portion rotates about the longitudinal axis. The proximal body has a longitudinal slide slot. The guide tube houses and secures the elongate member within the introducer assembly in the ready mode. Additionally, the slide collar is slidably disposed in the guide tube's longitudinal slide slot.

The slide collar has a grip, a slide post, and a centered capture structure. The slide collar is disposed so that the grip may be accessed and manually moved from outside the guide tube, the slide post is movably slidable within the slide slot, and the centered capture structure is advanceable centered about the longitudinal axis as the slide post is moved slidably within the slide slot.

Each of the proximal connector assembly and the distal connector assembly has roles relating to the elongate member. The proximal connector assembly may be detachably nested within the centered capture structure and is connected to the elongate member to securely hold the elongate member in longitudinal alignment with the longitudinal axis. The distal connector assembly may be detachably nested within the distal portion of the guide tube and is connectable both to the tubular-receiving structure and the proximal connector assembly.

To convert the introducer assembly from its ready mode to its introduced mode, the distal connector assembly first is connected to the tubular-receiving structure so that the distal connector assembly may guide the elongate member via a longitudinal passageway through the distal connector assembly into the connected tubular-receiving structure as the elongate member is advanced by manually advancing the slide collar toward the distal portion of the guide tube. Once the elongate member is sufficiently advanced for the proximal connector assembly to be connected to the distal connector assembly, the distal connector assembly rotates together with the distal portion to rotatably connect the distal connector assembly with the proximal connector assembly. As that connection is secured, a secure interim assembly is created comprising the fully advanced elongate member as guided through the passageway within the distal connector assembly and held securely by the proximal connector assembly and the connection of the proximal and distal connector assemblies.

The introducer assembly may be converted from the introduced mode to the detached mode by withdrawing the guide tube from the secure interim assembly. The guide tube detaches from the secure interim assembly leaving the elongate member disposed within the tubular-receiving structure. The proximal connector assembly detaches from its nesting engagement within the centered capture structure and the distal connector assembly detaches from its nesting engagement within the distal portion of the guide tube. The guide tube, as detached, may then be discarded, or disposed of, if the particular use does not require the retraction of the elongate member. However, if the particular use requires retraction of the elongate member, the guide tube may be retained and reattached to allow for retraction.

It is contemplated that the introducer assembly may be used in medical situations or non-medical situations. The introducer assembly may be used non-medically to introduce elongate members such as probes, sensors, cameras, light sources, or other non-medical elongate members into bores, pipes, conduits, tubes, tight cavities, and the like. Examples of non-medical uses include, but are not limited to, detecting decay in trees, or confirming visually the presence of harmful insects, inspecting a machine for defects using borescopes introduced into cavities within the machine, filming and observing bee activity by introducing infrared cameras into a beehive, and any other non-medical situation where an elongate member may be introduced into and/or retracted from a subject structure or body.

There are numerous medical uses requiring introduction and/or retraction of medical instruments into a patient's body or into a medical device or component outside a patient's body. Again, by way of example and not to be limiting, it may be beneficial and cost-effective to use the guide tube to insert and/or retract a medically-related elongate member, such as a guide wire, an endoscope, an angioscope, a hysteroscope, a gastroscope, a flexible telescope for colonoscopies, bronchoscope, a cystoscope, probes for illumination, probes for pinpoint medication or treatment delivery, probes for inflation gas delivery, fiber optics, and any of numerous other devices or instruments that are elongate and may be inserted and/or retracted. It is contemplated that, armed with the disclosure herein, persons of ordinary skill in the art could fashion guide tubes, disposable or not, to advance and/or retract such devices or instruments without undue experimentation.

Additionally, an introducer system for introducing an elongate member into a tubular-receiving structure may combine an adapter and an introducer assembly that has a ready mode, an introduced mode, and a detached mode. The adapter may comprise a main line, an entry port, an exit port, a branching line, and a side port, wherein the main line is tubular and has the entry port and the exit port disposed at opposite ends of the main line. The branching line communicates with the main line and has the side port. As described, the adapter is a 3-port adapter that may be configured to allow uninhibited flow of a fluid through the exit port, the main line, the branching line, the side port, and into and out of one or more tubular-receiving structures.

One implementation of an exemplary introducer system may have the entry port connected to the distal connector assembly, the exit port may be connected to the tubular-receiving structure, the side port is connected to a second tubular-receiving structure. With this embodiment of the introducer system, the elongate member passes through the entry port into the main line of the adapter as the elongate member is advanced by advancing the slide collar toward the distal portion.

In another exemplary embodiment of the adapter, the main line may comprise a needle-free connector (NFC) at the entry port, a hub, a tube body, and an exit connector at the exit port (e.g., a luer designed to connect to an extension set connectable to a dialysis cycler). This exemplary embodiment may be used with an introducer assembly having a proximal connector assembly comprising a Subminiature A (SMA) fiber connector and a ferrous ring that may connect magnetically to an optical connector receiving light through a light transmission cable from a light engine that delivers non-ultraviolet light to a fiber optic via the SMA fiber connector so that the fiber optic may provide targeted radial emission of the light to disinfect the adapter and/or the extension set connected to a dialysis cycler.

Some exemplary embodiments employ an annular snap-fit joint to rotatably connect the proximal body with the distal portion of the guide tube. The snap-fit joint need not be fully annular so long as adequate rotation is enabled by the snap-fit joint. Also, many snap-fit joints have male protrusions that rotatably fit within female recesses, and if such snap-fit joints are used the male protrusion may be part of the proximal body or the distal portion.

Other exemplary embodiments may comprise various types of tubular-receiving structures such as catheters, extension or transfer sets, tubing, tubes, and the like.

Yet another exemplary embodiment may comprise a fiber optic as the elongate member prepared to optimize targeted radial emission of non-ultraviolet light to reduce, inhibit, prevent, or eliminate infectious agents in, on, or around a targeted tubular-receiving structure.

Still another exemplary embodiment achieves uniform radial transmission wherein the radial emission portion of the fiber optic has substantially equivalent intensity over the length of a radial emission portion along the fiber optic.

In another exemplary embodiment, the introducer system connects to a dialysis catheter (whether used for hemodialysis or peritoneal dialysis) with or without an extension set.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the present disclosure will be described with additional specificity and detail through use of the accompanying drawings in which:

FIG. 8A is a perspective view of the fiber optic assembly (configured to seat within the centered annular cylinder) showing a SMA fiber connector (SubMiniature A connector), a ferrous ring, and a proximal luer. FIG. 8B is a perspective connector end view of the fiber optic assembly. FIG. 8C is a perspective luer end view of the fiber optic assembly.

REFERENCE NUMERALS

Figure 1:
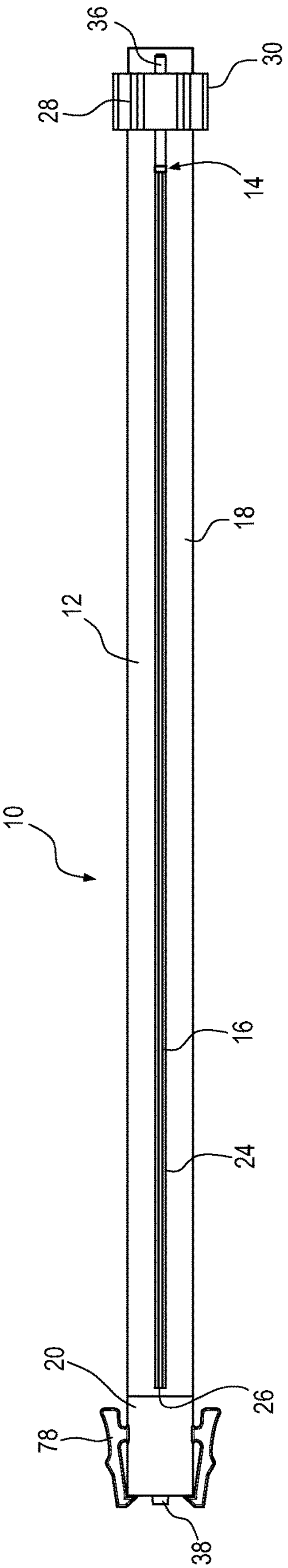
FIG. 1 is a top plan view of an exemplary introducer assembly depicted in a ready mode, fully assembled and ready for use, the ready mode being a configuration of the introducer assembly during transport and/or storage typically.

| | |
|---|---|
| introducer assembly 10 | guide tube 12 |
| elongate member assembly 14 | elongate member 16 |
| proximal body 18 | distal portion 20 |
| longitudinal axis 22 | slide slot 24 |
| stop 26 | slide collar 28 |
| grip 30 | slide post 32 |
| centered annular cylinder 34 | proximal connector assembly 36 |
| distal connector assembly 38 | snap-fit joint 40 |
| fiber optic 42 | SMA fiber connector 44 (SubMiniature A connector) |
| ferrous ring 46 | proximal luer 48 |

-continued

| | |
|---|---|
| distal connector 50 | connector attachment ring 52 |
| distal luer 54 | longitudinal passageway 56 |
| luer attachment ring 58 | rotation-inhibiting feature 60 |
| raised rib 62 | groove(s) 64 |
| male extension 66 | female recess 68 |
| protrusion 70 | furrow 72 |
| annular ridge 74 | annular furrow 76 |
| lever clamps 78 | inner surface 80 |
| breadth 82 | inward curved extension 83 |
| 3-port adapter 84 | tubular-receiving structure 86 |
| main line 88 | branching line 90 |
| entry port 92 | exit port 94 |
| side port 96 | introducer system 98 |
| needle-free connector (NFC) 100 | hub 102 |
| tube body 104 | exit connector 106 |
| tubing bond pocket (tubing pocket) 108 | branching stub 110 |
| branch tubing 112 | side port luer 114 |
| pinch clamp 116 | handling grip 118 |
| secure interim assembly 120 | optical connector 122 |
| extension set 124 | catheter 126 |
| rotation arrows RA | |

DETAILED DESCRIPTION

Exemplary embodiments of the present disclosure will be best understood by reference to the drawings, wherein like parts are designated by like numerals throughout. It will be readily understood that the components of the exemplary embodiments, as generally described and illustrated in the Figures herein, could be arranged, sized, and designed in a wide variety of different configurations. Thus, the following more detailed description of the exemplary embodiments of the apparatus, system, and method of the present disclosure, as represented in FIGS. 1 through 15, is not intended to limit the scope of the invention, as claimed, but is merely representative of exemplary embodiments.

The phrases “attached to”, “secured to”, and “mounted to” refer to a form of mechanical coupling that restricts relative translation or rotation between the attached, secured, or mounted objects, respectively. The phrase “slidably attached to” refers to a form of mechanical coupling that permits relative translation, respectively, while restricting other relative motions. The phrase “attached directly to” refers to a form of securement in which the secured items are in direct contact and retained in that state of securement.

The term “abutting” refers to items that are in direct physical contact with each other, although the items may not be attached together. The term “integrally formed” refers to a body that is manufactured as a single piece, without requiring the assembly of constituent elements. Multiple elements may be formed integral with each other, when attached directly to each other to form a single work piece.

The word “exemplary” is used herein to mean “serving as an example, instance, or illustration.” Any embodiment described herein as “exemplary” is not necessarily to be construed as preferred or advantageous over other embodiments. While the various aspects of the embodiments are presented in drawings, the drawings are not necessarily drawn to scale unless specifically indicated.

For exemplary methods or processes of the invention, the sequence and/or arrangement of steps described herein are illustrative and not restrictive. Accordingly, it should be understood although steps of various processes or methods may be shown and described as being in a sequence or temporal arrangement, the steps of any such processes or methods are not limited to being carried out in any one sequence or arrangement, absent an indication otherwise.

Indeed, the steps in such processes or methods generally may be carried out in various sequences and arrangements while still falling within the scope of the present invention.

Figure 2:
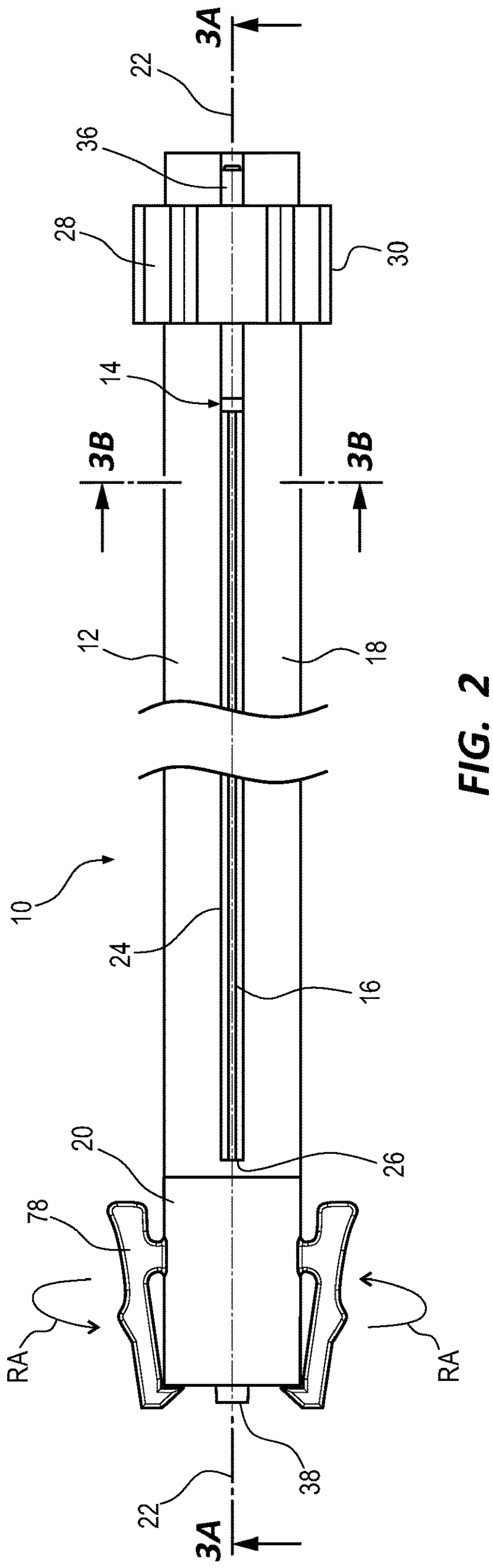
FIG. 2 is an enlarged broken view of the exemplary introducer assembly of FIG. 1 showing the component parts of the introducer assembly (including a disposable guide tube and an elongate member) and a vertical section designation along Line 3A-3A (that includes the longitudinal axis for the disposable guide tube and the elongate member) and a vertical cross-section line along Line 3B-3B.

Turning to FIGS. 1 and 2, an exemplary introducer assembly 10 is depicted in a ready mode, fully assembled and ready for use, the ready mode being a configuration of the introducer assembly 10 during shipping and/or storage typically. The exemplary introducer assembly 10 comprises two principal components, a disposable guide tube 12 and an elongate member assembly 14.

The guide tube 12 may be disposable and may be constructed in dimensions ergonomically complementary to its intended use and/or target users and may be made of any suitable material that is cost-effective and complementary to its use. For example, and not limited to this example, the guide tube 12 may be constructed of lightweight materials with a larger diameter and larger movable parts balanced to fit comfortably in a person's hand that may have limited dexterity, poor vision, and/or some other limiting characteristic(s) that may otherwise inhibit proper use of a less well-sized or smaller guide tube 12. Furthermore, the elongate member assembly 14, as housed within the guide tube 12 while in a ready mode, may be advanced within the guide tube 12 to an introduced mode wherein any of numerous types of elongate members 16 is introduced into a desired disposition such as within a tubular structure (e.g., a bore, tubing, a conduit, a catheter, and the like). Because elongate members 16 exist in various sizes and rigidity, the guide tube 12 may require larger/smaller diameters, longer/shorter lengths, and larger/smaller other components to accommodate the selected elongate member 16. For example, if the elongate member 16 is a borescope used within a larger diameter bore in a mechanical device the diameter and/or length of the guide tube 12 likely may be larger than it would need to be for an elongate member 16 that is a cystoscope used to see inside a person's bladder.

It is contemplated that the introducer assembly 10 may be used in medical situations or non-medical situations. By way of example and not to be limiting, the introducer assembly 10 may be used non-medically to introduce elongate members 16 such as probes into bores to detect decay in trees or to confirm visually the presence of harmful insects, borescopes into cavities within a machine to inspect the machine for defects, infrared cameras into a beehive to film and observe bee activity, and any other non-medical situation where an elongate structure, probe, sensor, camera, light source, or the like may be introduced into and/or retracted from a subject structure or body.

Additionally, there are numerous medical uses requiring introduction and/or retraction of medical instruments into a patient's body or into a medical device or component. Again, by way of example and not to be limiting, it may be beneficial and cost-effective to use the guide tube 12 to insert and/or retract a medically-related elongate member 16, such as a guide wire, an endoscope, an angioscope, a hysteroscope, a gastroscope, a flexible telescope for colonoscopies, bronchoscope, a cystoscope, probes for illumination, probes for pinpoint medication or treatment delivery, probes for inflation gas delivery, fiber optics, and any of numerous other devices or instruments that are elongate and may be inserted and/or retracted. It is contemplated that, armed with the disclosure herein, persons of ordinary skill in the art could fashion guide tubes 12, disposable or not, to advance and/or retract such devices or instruments without undue experimentation.

For conciseness, the introducer assembly 10 described herein is intended to be a representative, exemplary embodiment. The spirit and scope of the invention disclosed includes each embodiment contemplated for use in medical and non-medical contexts that enable those skilled in the art armed by this disclosure. Consequently, the spirit and scope of the invention disclosed should not be limited to the exemplary, medical-context embodiments described herein. The representative, exemplary embodiment(s) of the introducer assembly 10 described herein has medical context where the elongate member 16 is an optical fiber to be introduced into a tubular-receiving structure such as a catheter and/or an adapter and serves as a representative description of other embodiments rather than describing each embodiment contemplated for use in medical and non-medical contexts.

To simplify the description of the invention in this disclosure, the introducer assembly 10 of FIGS. 1 and 2 is a representative example of all introducer assemblies contemplated herein comprising a guide tube 12 and an elongate member assembly 14. The guide tube 12 may be disposable or not but is particularly suitable for disposability because it may be removed from the elongate member assembly 14. Guide tube 12 comprises a proximal body 18 and a distal portion 20 and has a longitudinal axis 22 about which the distal portion 20 may be rotated relative to the proximal body 18 as depicted by rotation arrows RA in FIG. 2. The proximal body 18 has a longitudinal slide slot 24 with a stop 26. As mentioned above, the dimensions and the materials with which the guide tube 12 is made may be determined to accommodate whatever type of elongate member 16 is selected to be used.

The component parts of introducer assembly 10 (as best shown in the section view of FIG. 3A), in addition to guide tube 12 described above, comprise a slide collar 28 having a grip 30, a slide post 32 and a centered capture structure depicted as a centered annular cylinder 34 (centered about the longitudinal axis 22), a proximal connector assembly 36 configured to nest within the centered annular cylinder 34, and a distal connector assembly 38 configured to nest rotatably with the distal portion 20. Additionally, an at least partially annular snap-fit joint 40 facilitates the rotation of a distal portion 20 relative to a proximal body 18 of the guide tube 12.

Figure 3A:
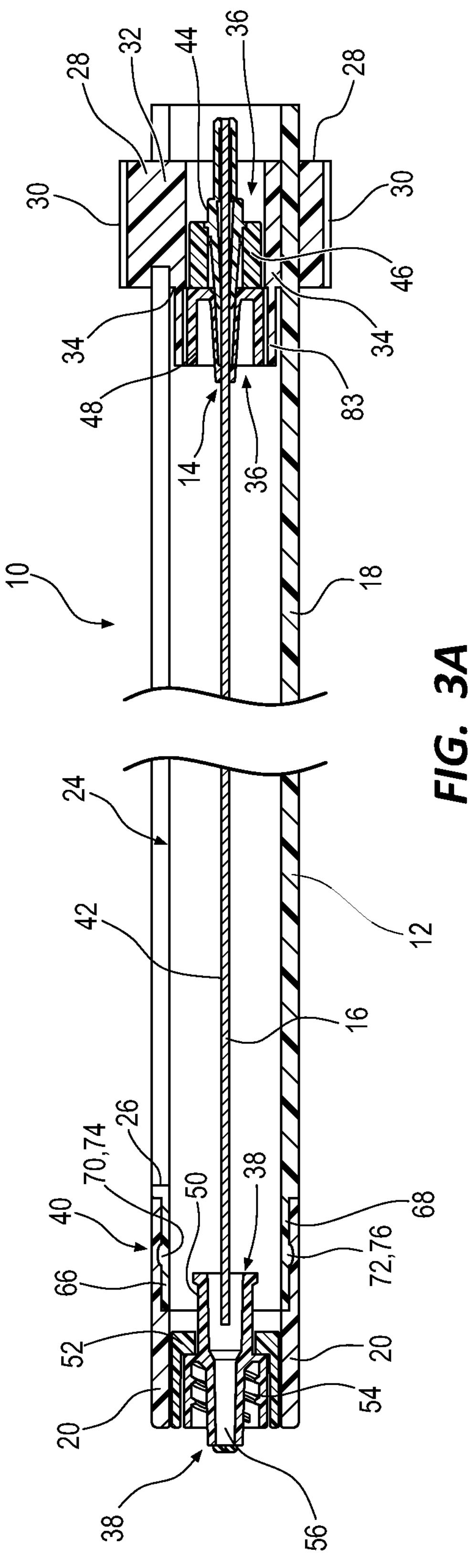
FIG. 3A is a vertical section side view of the exemplary introducer assembly of FIG. 2 along Line 3A-3A that better depicts the various component parts and showing the annular snap-fit joint that facilitates the rotation of a distal portion relative to a proximal body of the disposable guide tube.

The centered capture structure is depicted in FIG. 3A as a centered annular cylinder 34; however, the centered capture structure need not be annular or circular so long as it grasps or captures the proximal connector assembly 36 in a nesting engagement so that the elongate member assembly 14 advances longitudinally along the longitudinal axis 22. For example, the centered capture structure may be any of a number of structures that captures and secures the proximal connector assembly 36 during advancement of the slide collar 28 such as a partial cylinder, a hollow frustoconical structure (whether annular or partially annular), a rectangular tube or partially rectangular tube (if the transverse profile of the proximal connector assembly 36 fits therewithin and is captured), a non-circular tube or partial non-circular tube (if the transverse profile of the proximal connector assembly 36 fits therewithin and is captured), or any other capturing structure that secures and advances the proximal connector assembly 36 during the advancement of the sliding collar 28 and may easily release the proximal connector assembly 36 when guide tube 12 is removed from the elongate member assembly 14. Because the transverse profile of the proximal connector assembly 36 may have almost any shape, those skilled in the art, armed with this disclosure, may easily fashion a centered capture structure without undue experimentation. For brevity, the drawings depict a centered annular cylinder 34, but the scope of the invention should not be limited to that structure.

FIG. 3A, a vertical section side view of the exemplary introducer assembly 10 of FIG. 2 along Line 3A-3A, depicts the various component parts while disposed in the ready mode. The ready mode is the configuration that would be most suitable for shipment and storage. In fact, the introducer assembly 10 may be pre-sterilized and packaged to maintain sterility during shipment and storage. In the ready mode the slide collar 28 is slidably connected to the guide tube 12 such that the grip 30 is accessible to the user while the user holds the guide tube 12, the slide post 32 slidably engages the slide slot 24, and the centered annular cylinder 34 is centered about the longitudinal axis 22 and may travel along the longitudinal axis 22 as the grip 30 is advanced from the ready mode to the introduced mode.

Figure 8C:
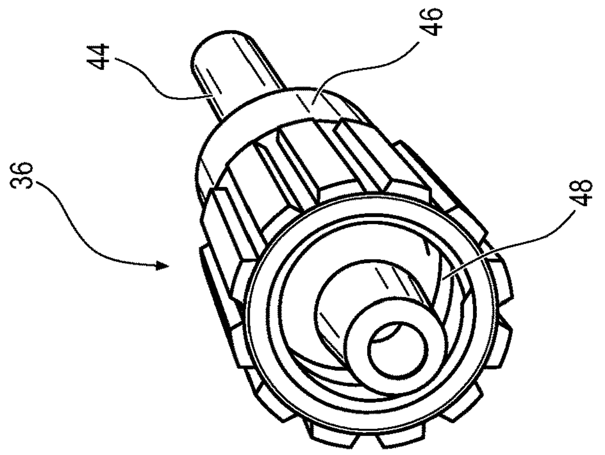
FIGS. 8A-8C are various views of an exemplary fiber optic assembly.
Figure 8B:
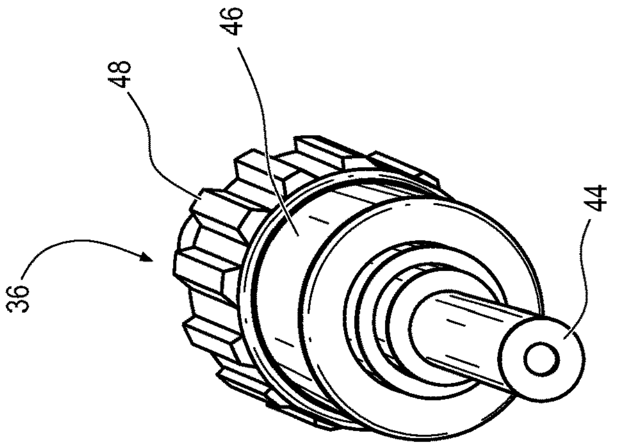
Figure 8A:
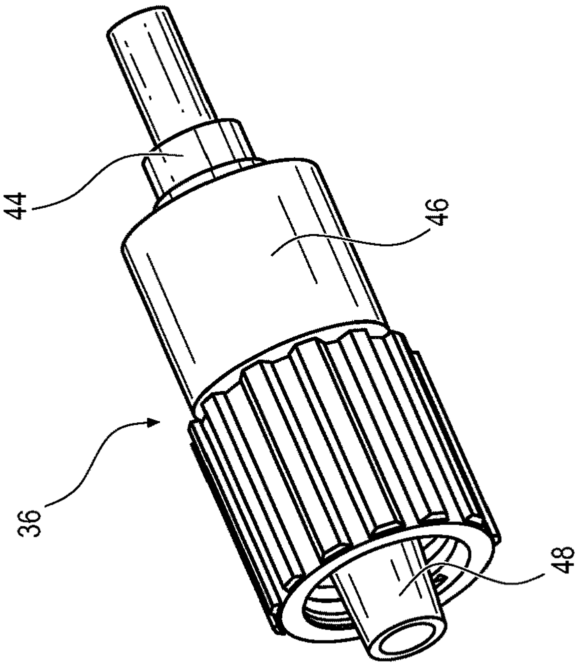

As depicted, the proximal connector assembly 36 nests within the centered annular cylinder 34 and holds the elongate member 16; namely, a fiber optic 42 in the depicted exemplary embodiment, to extend along the longitudinal axis 22. For a fiber optic 42, FIGS. 8A-8C show various views of the proximal connector assembly 36 that comprises an SMA fiber connector 44 (SubMiniature A connector) that securely grasps or holds the proximal end of the fiber optic 42 and transfers light from a light source (not shown) to the fiber optic 42 for axial propagation along the fiber optic 42, a ferrous ring 46, and a proximal luer 48. FIG. 8A is a perspective view of the proximal connector assembly 36 showing the proximal end of the SMA fiber connector (SubMiniature A connector) depicted in the uppermost right portion of the figure. FIG. 8B is a perspective connector end view of the proximal connector assembly 36 showing the proximal end of the SMA fiber connector (SubMiniature A connector) depicted in the foreground of the figure. FIG. 8C is a perspective luer end view of the proximal connector assembly 36 showing the luer threads depicted in the foreground of the figure. When the elongate member 16 is a fiber optic 42 the proximal connector assembly 34 and the fiber optic 42 form the elongate member assembly 14 (best shown in FIG. 4) which is sometimes referred to herein as a fiber optic assembly.

The ferrous ring 46 facilitates magnetic securement of the proximal connector assembly 36 to the light source (not shown). The proximal luer 48 is configured to connect in secure engagement with the distal connector assembly 38 when the distal portion 20 is rotated to couple together the proximal connector assembly 36 and the distal connector assembly 38 in threaded engagement. Stop 26 prevents the distal portion 20 from advancing too far and/or from over rotating and damaging the distal connector assembly 38. The combination of advancing the slide collar 28 and rotating the distal portion 20 to couple together the proximal connector assembly 36 and the distal connector assembly 38 moves the introducer assembly 10 from the ready position where the elongate member 16 is housed within the guide tube 12 to the introduced mode where the elongate member 16 is advanced fully through and extends from the distal connector assembly 38.

The distal connector assembly 38 (also shown in FIG. 5 and in the end view of FIG. 6 as nested in the distal portion 20) comprises a distal connector 50 and a connector attachment ring 52. For the representative embodiment where the elongate member 16 is a fiber optic 42, the distal connector 50 is a distal luer 54 with a longitudinal passageway 56 through which the fiber optic 42 may extend, and the connector attachment ring 52 is a luer attachment ring 58 having a rotation-inhibiting feature 60. The distal luer 54 with a longitudinal passageway 56 may be any suitable luer that facilitates the operation of the introducer assembly 10 depending upon the type of elongate member 16 selected. The depicted exemplary distal luer 54 is a female-to-male luer that may be coupled with the proximal luer 48 of the proximal connector assembly 36; however, other configurations may be suitable (including for example, a male-to-female luer), and those skilled in the art, armed with this disclosure, may utilize other luers or connectors to operate in other configurations.

Figure 6:
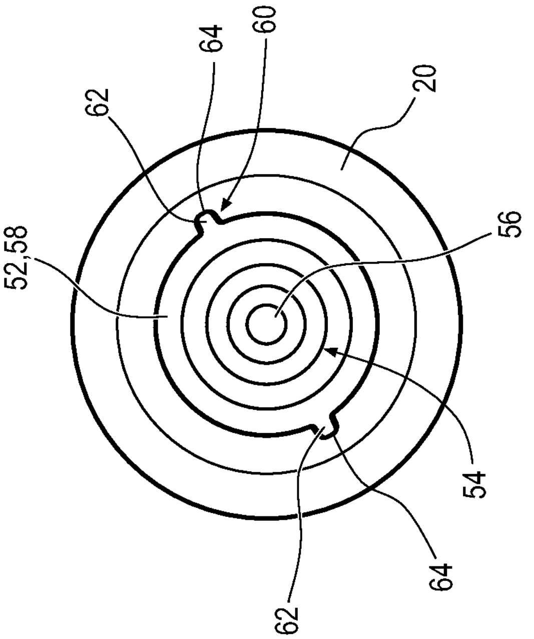
FIG. 6 is an end view of the exemplary introducer assembly of FIG. 1 showing the distal luer assembly seated within an exemplary rotatable distal portion of a guide tube.
Figure 5:
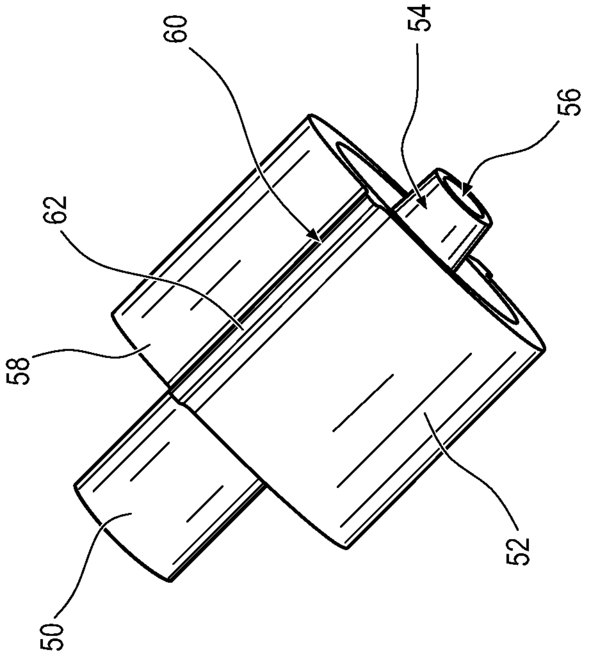
FIG. 5 is a perspective view of an exemplary distal connector assembly comprising a distal connector and a connector attachment ring wherein the connector is a luer.
Figure 7:
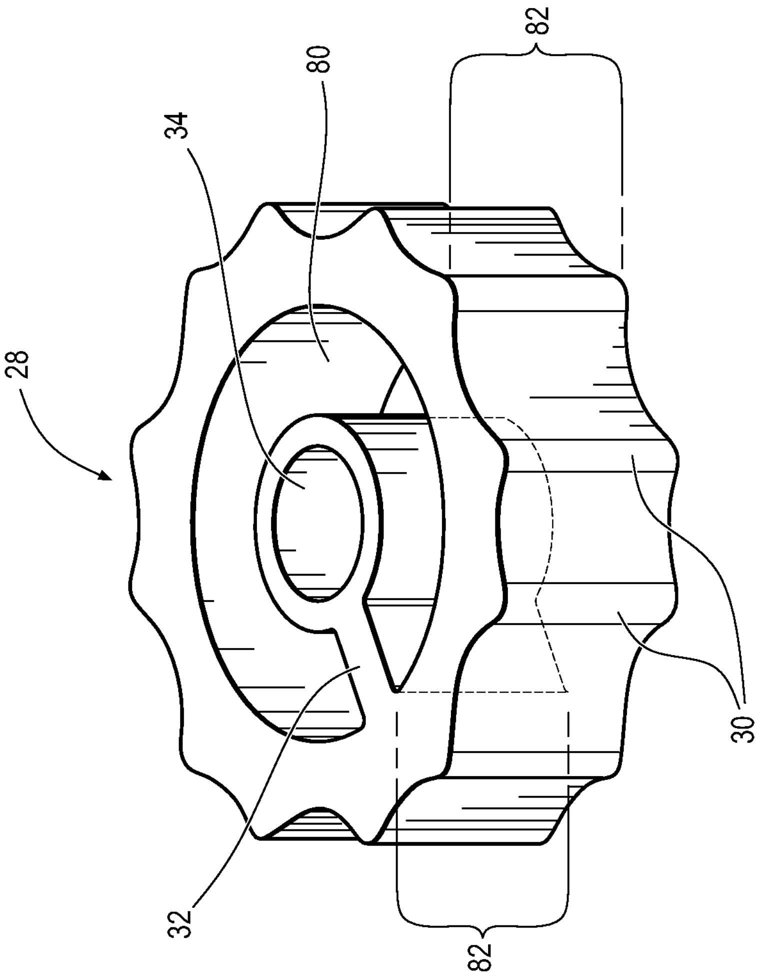
FIG. 7 is a perspective view of an exemplary slide collar (shown also in FIGS. 1-4) depicting a slide post that suspends a centered capture structure (a centered annular cylinder as depicted).

The exemplary distal luer 54 may be press-fit to nest within the luer attachment ring 58 with the rotation-inhibiting feature 60 as depicted in FIG. 5. Alternatively, the distal connector assembly 38 may be custom made with the connector attachment ring 52 formed integrally with or attached to the distal connector 50. The exemplary rotation-inhibiting feature 60 of the luer attachment ring 58, as depicted in FIGS. 5 and 6, has at least one raised rib 62 that slides into rotation-inhibiting engagement with corresponding groove(s) 64 in the interior wall of the distal portion 20. Other types of rotation-inhibiting features 60 are also contemplated but not shown for the sake of brevity; by way of example and not to be limiting, the connector attachment ring 52 may have groove(s) while the interior wall of the distal portion 20 may have corresponding raised rib(s) or raised bead(s) or the connector attachment ring 52 may have a flat side that corresponds to a flat surface in the interior wall of the distal portion 20 or the connector attachment ring 52 may have a non-circular cross section the corresponds to a non-circular cross section in the interior wall of the distal portion 20.

The annular snap-fit joint 40 that facilitates the rotation of a distal portion 20 relative to a proximal body 18 of the guide tube 12 also is best depicted in FIG. 3A. The annular snap-fit joint 40 comprises a male extension 66, a female recess 68, a protrusion 70, and a furrow 72. The protrusion 70 may be of any suitable type (e.g., an annular ring or ridge, a portion or portions of an annular ring or ridge, a bead or beads, a post, or posts, and the like) may be disposed on the exterior of the male extension 66 or on the interior wall of the female recess 68. The furrow 72 may be of any suitable type corresponding to the type of protrusion 70 (e.g., an annular furrow, a portion or portions of an annular furrow, a bead-receiving channel, a post receiving channel, or the like). The representative embodiment depicted in FIG. 3A is an annular snap-fit joint 40 comprising a male extension 66 of the proximal body 18 having an annular ridge 74 and a female recess 68 of the distal portion 20 having an annular furrow 76. The configuration of the representative embodiment enables the rotation of the female recess 68 of the distal portion 20 about the male extension 64, wherein the annular ridge 74 travels within the annular furrow 76. Of course, the configuration could be reversed where the female recess 68 is part of the proximal body 18 and the male extension 64 is part of the distal portion 20.

Additionally, as depicted in FIG. 3A, the annular snap-fit joint 40 permits a complete rotation of the distal portion 20 about the proximal body 18 unless otherwise halted. There are numerous ways to control the rotation of the distal portion 20 about the proximal body 18. One example of controlling the rotation is described above where the stop 26 on the slide slot 24 will inhibit further longitudinal advancement of the elongate body 16 to end further threaded engagement during rotation. Another example may be to use one or more partial annular ridges 74, beads, or posts that travel within one or more partial annular furrow 76 wherein the rotation is controlled by the length of the partial annular furrow(s) 76.

Figure 4:
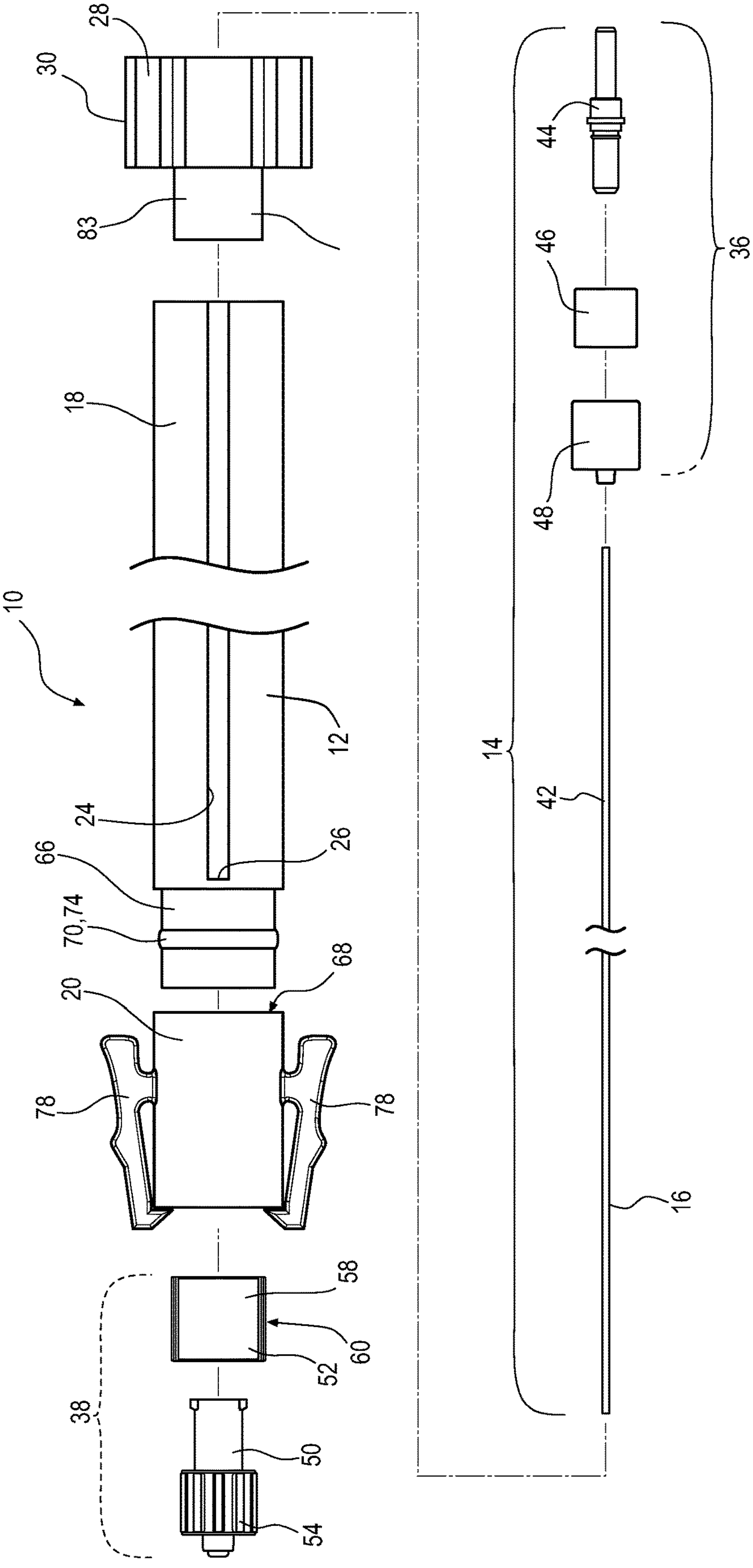
FIG. 4 is an exploded broken view of the disposable introducer and the elongate member, respectively, in which the exemplary elongate member is an exemplary fiber optic assembly.

FIGS. 1, 2, and 4 depict an alternative embodiment of the introducer assembly 10 that show optional lever clamps 78 to hold securely the distal connector assembly 38 within distal portion 20 to eliminate the distal connector assembly 38 from being inadvertently dislodged during shipping/storage, user handling, and user rotation manipulation. Additionally, the lever portion of the lever clamps 78 may be grasped by the user to apply the rotational torque needed to rotate the distal portion 20. Additionally, FIG. 4, depicting an exploded broken view of an exemplary disposable introducer assembly 10 for an exemplary fiber optic 42, suggests how the component parts may be assembled.

Figure 3B:
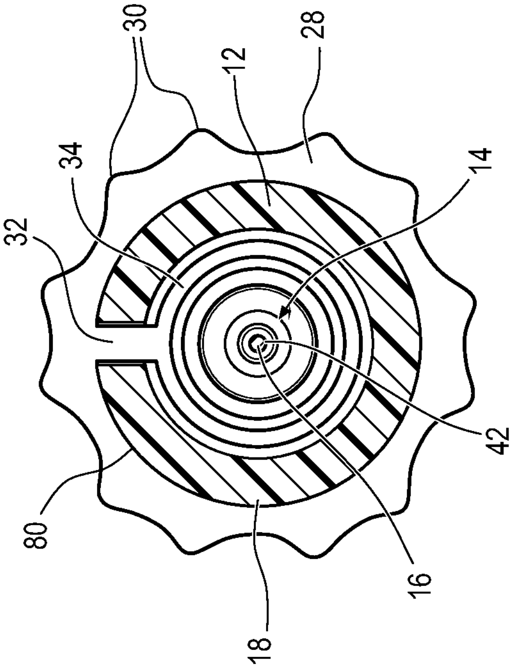
FIG. 3B is a vertical cross-section view of the exemplary introducer assembly of FIG. 2 along Line 3B-3B that better depicts the component parts looking towards an exemplary slide collar.

FIG. 3B is a vertical cross-section view of the exemplary introducer assembly 10 of FIG. 2 along Line 3B-3B that depicts the component parts looking towards an exemplary slide collar 28. The slide collar 28 depicted (see also FIG. 7) has an annular structure with grip 30 along its outermost surface and a relatively smooth inner surface 80 that has a diameter slightly larger than the diameter of the guide tube 12. The grip 30 and the slide post 32 have breadth 82 sufficient to inhibit twisting of the slide collar 28 as it is advanced to significantly reduce or eliminate pinch points and binding between the slide collar 28 and the guide tube 12 thereby providing a relatively smooth advancement of the slide collar 28 within the slide slot 24. To provide additional stability eliminating pinch points and binding, slide collar 28 may also comprise an inward curved extension 83, as shown best in FIG. 3A, that may be annular or partially annular.

Figure 10:
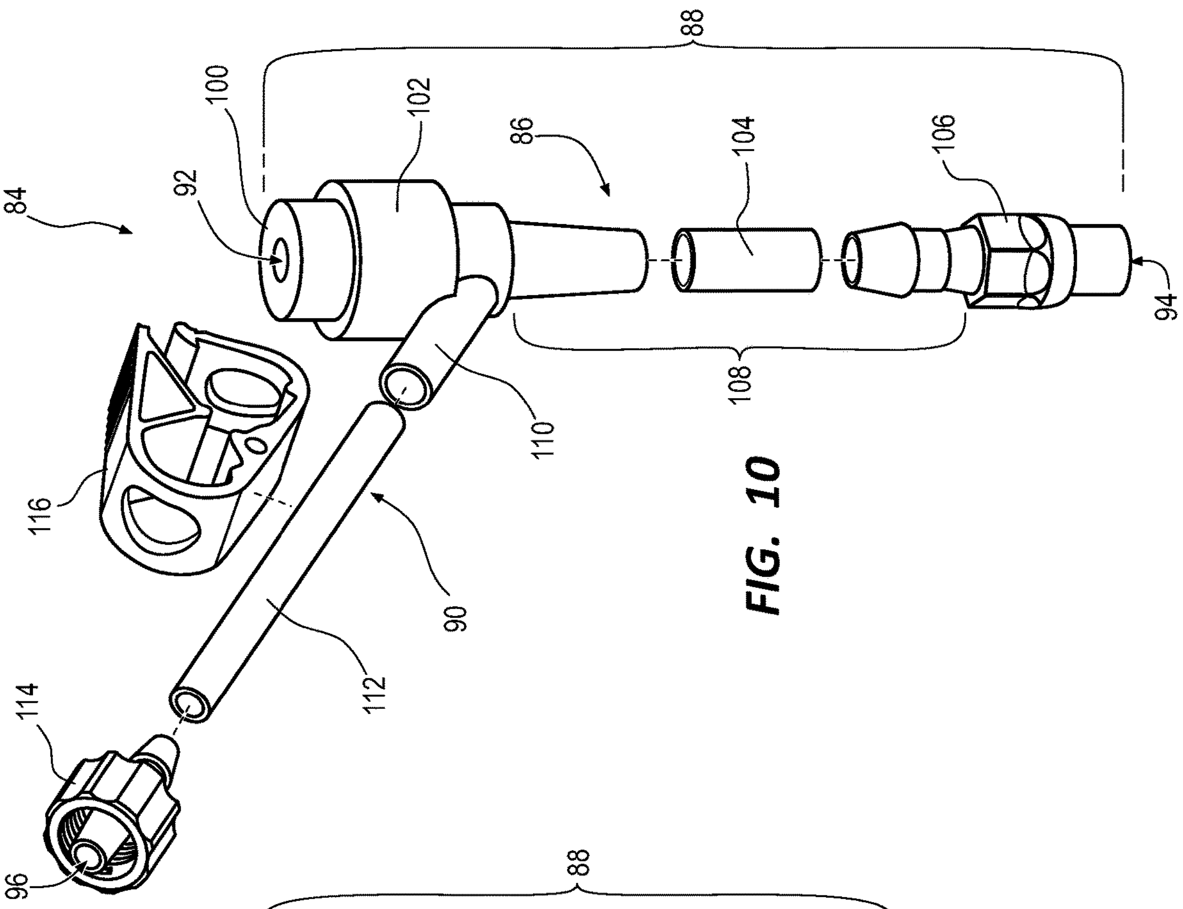
FIG. 10 is an exploded perspective view of the exemplary 3-port adapter of FIG. 9 showing the individual component parts thereof.
Figure 9:
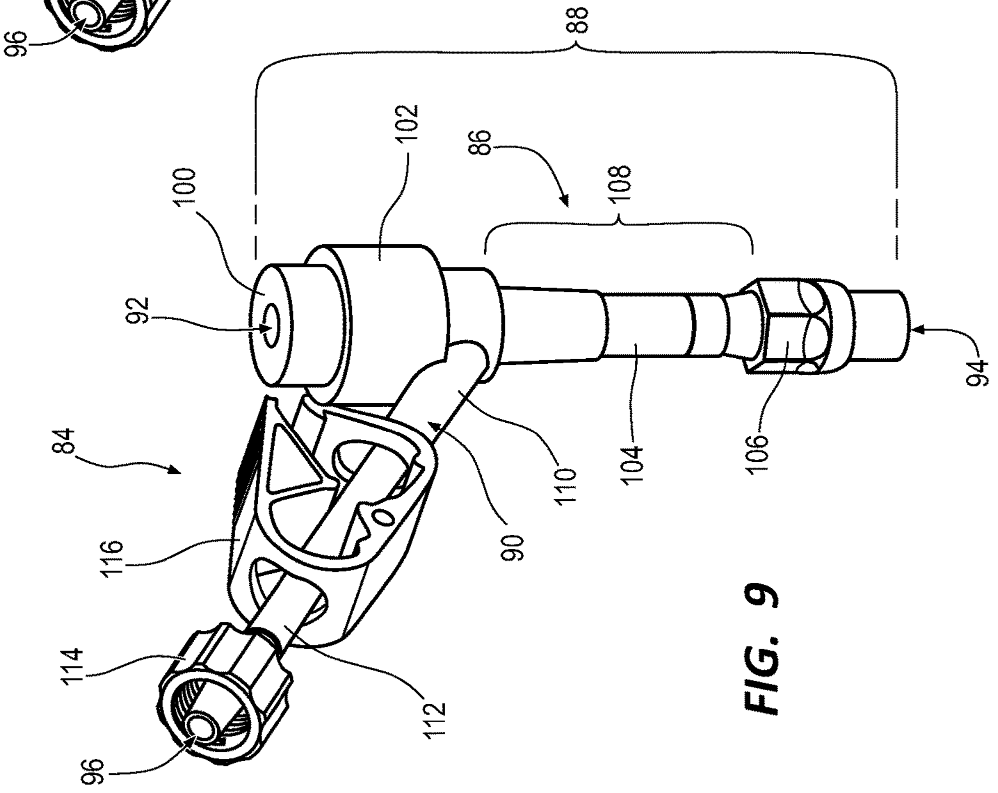
FIG. 9 is a perspective view of an exemplary 3-port adapter for connecting intermediate between the introducer assembly and a tubular-receiving structure.
Figure 14:
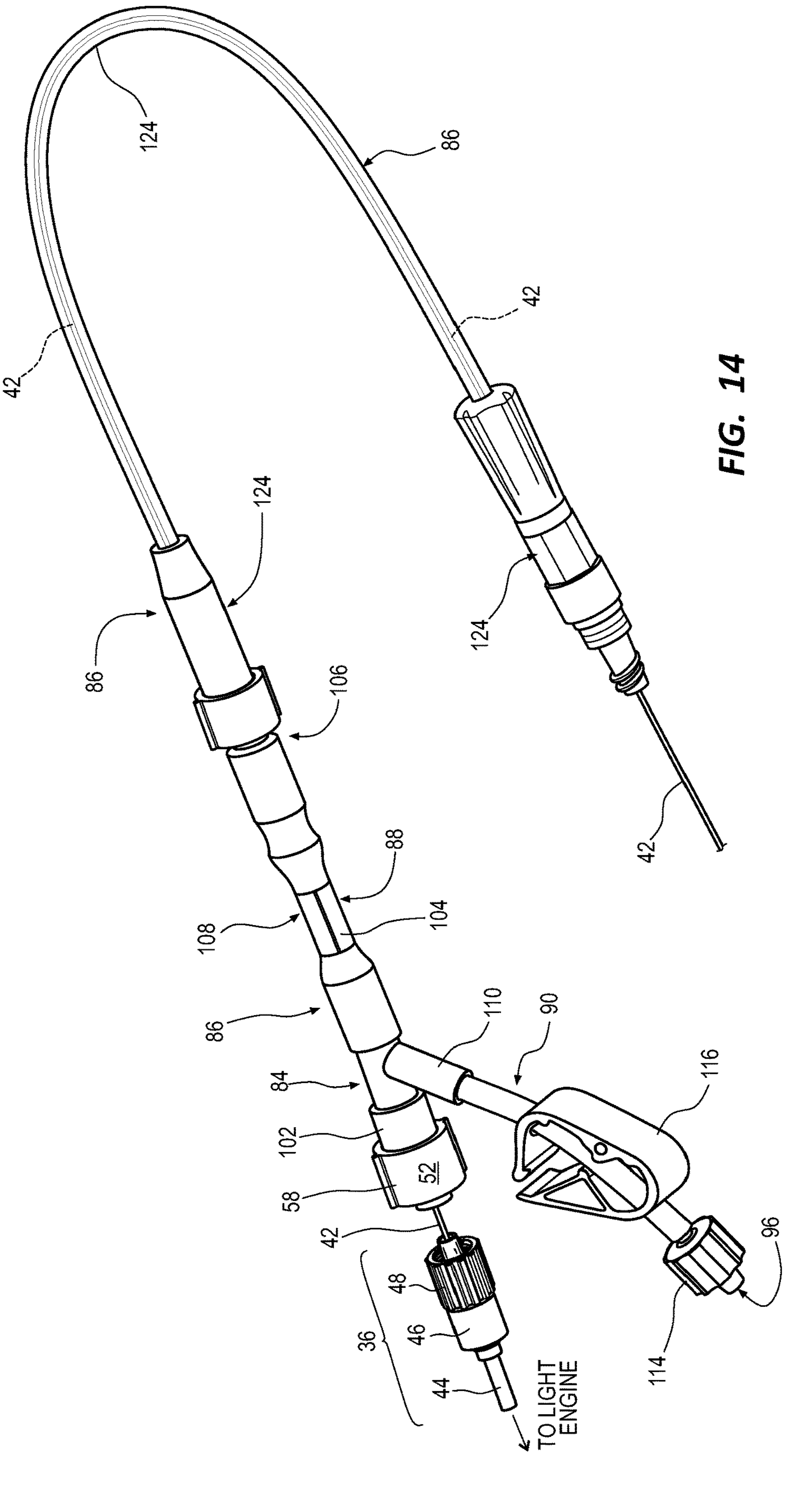
FIG. 14 is a partially exploded perspective view showing the 3-port adapter connected to an exemplary tubular-receiving structure; namely, an extension set, with the proximal connector assembly (a fiber optic assembly) disconnected and slightly withdrawn to reveal a portion of the fiber optic otherwise partially enclosed within and extending beyond the extension set.
Figure 15:
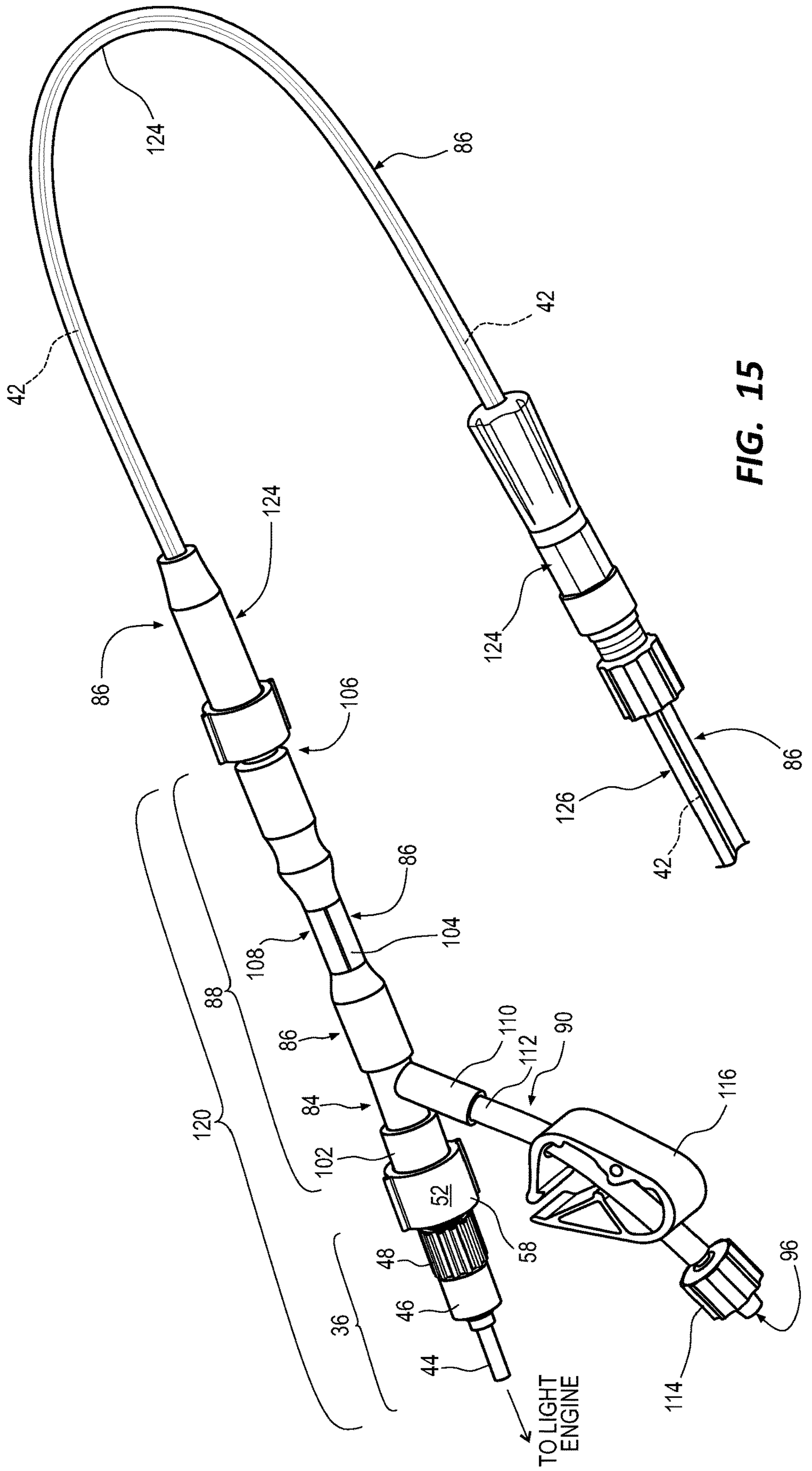
FIG. 15 is a perspective view of an exemplary connection assembly of the components shown in FIG. 14 fully assembled and attached to an exemplary catheter.

FIGS. 9-10 depict an exemplary 3-port adapter 84 for connecting intermediate between the introducer assembly 10 and a tubular-receiving structure 86 (see FIGS. 14-15). Referring to FIG. 10, the exploded perspective view of the exemplary 3-port adapter 84 best shows the individual component parts of the 3-port adapter 84 which comprises a main line 88 and a branching line 90. The main line 88 is tubular and has the entry port 92 and the exit port 94 disposed at opposite ends of the main line 88 and the branching line 90 communicates with the main line 88 and has the side port 96 forming a Y-connector or a T-connector. Because the main line 88 is tubular, the main line 88 itself is a tubular-receiving structure 86 as is any other tubular structure capable of receiving the elongate member 16 as it is advanced. The entry port 92 is connectable to the distal luer 54 of the elongate member assembly 14, the exit port 94 is connectable to a tubular structure (not shown), and the side port 96 is connectable to a second tubular structure (not shown). Hence, the 3-port adapter 84 when connected to the distal luer 54 becomes supplement to the introducer assembly 10 the combination of the introducer assembly and the 3-port adapter 84 creates an introducer system 98 that is connectable to the tubular-receiving structure 86 wherein the 3-port adapter 84 is disposed intermediate of the introducer assembly 10 and the tubular-receiving structure 86.

In the exemplary embodiment depicted in FIGS. 9 and 10, the main line 88 further comprises a needle-free connector (NFC) 100, a hub 102, a tube body 104, and an exit connector 106 (e.g., a luer designed to connect to extension tubing or an extension set connectable to a dialysis cycler). The main line 88, as assembled, may create an integrated tubing bond pocket 108 (tubing pocket) so that the elongate member 16 (e.g., fiber optic 42) may be introduced directly through the NFC 98 and tubing pocket 108, thereby minimizing the likelihood of the elongate member 16 getting snagged.

The branching line 90 comprises a tubular branching stub 110, branch tubing 112 and a side port luer 114 (e.g., a male luer as depicted). A pinch clamp 116 may be added to occlude the branch tubing 112 to provide fluid control.

Figure 11:
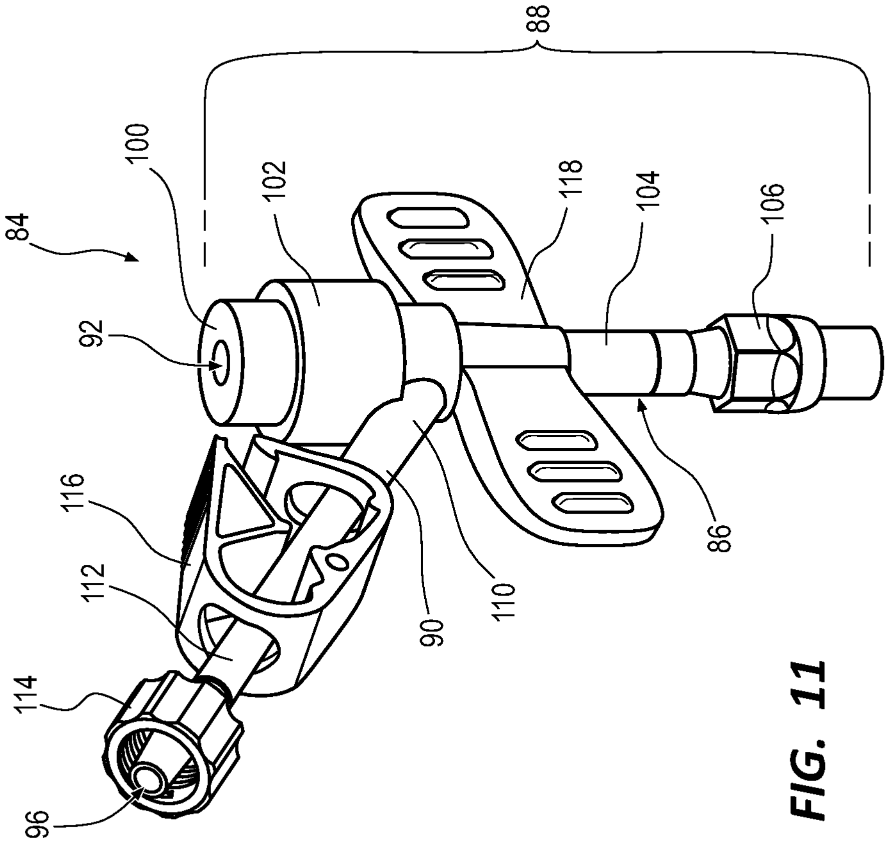
FIG. 11 is a plan view of another exemplary assembly of the 3-port adapter showing an exemplary handling grip attached to provide handling convenience.

FIG. 11 is a plan view of another exemplary assembly of the 3-port adapter 84 showing an exemplary handling grip 118 attached to provide handling convenience. 3-port adapters 84 may be small and difficult to handle without touching, and possibly contaminating, the region around the ports (entry port 92, exit port 94, and side port 96). The handling grip 118 may be of any suitable type so long as it provides a gripping surface that may be accessed without contaminating critical regions of the 3-port adapter 84. The handling grip 118 may be a clamshell attachment or may be molded onto the 3-port adapter, or it may be added to the handling grip 118 in any suitable manner that will not interfere with the operation of the 3-port adapter 84.

Figure 12:
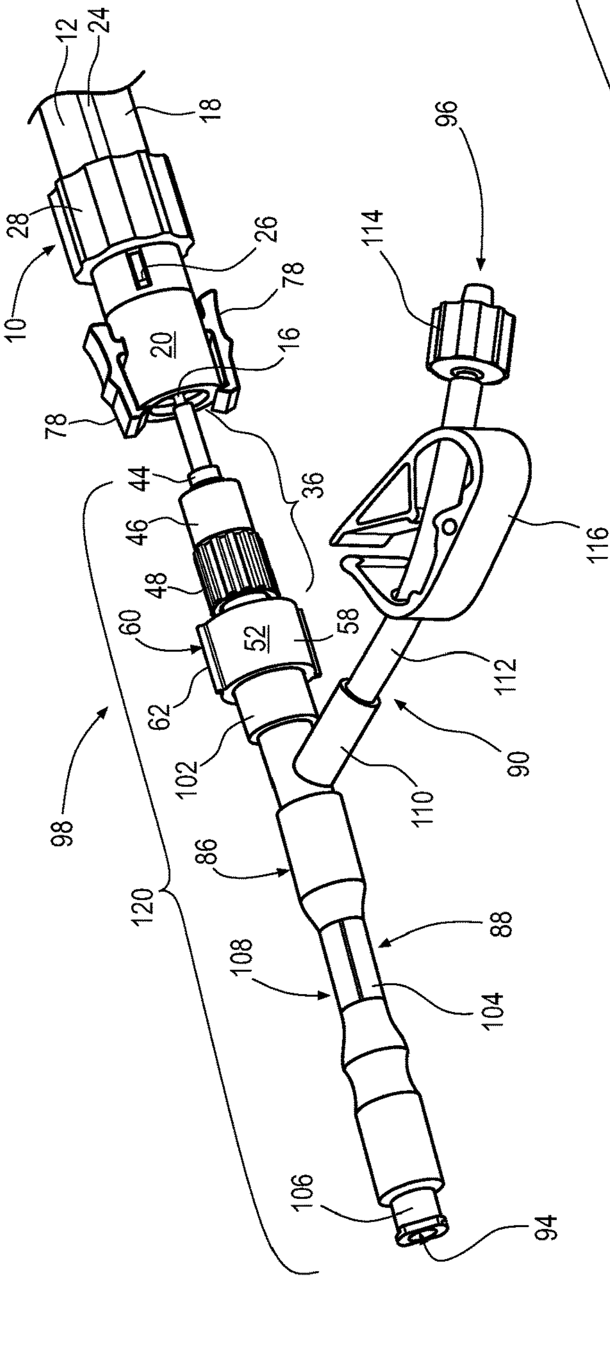
FIG. 12 is a plan view of an exemplary assembly of the 3-port adapter as connected and part of a secure interim assembly and being detached from the guide tube.

FIG. 12 is an exploded view of an exemplary secure interim assembly 120 comprising the 3-port adapter 84 as connected to and receiving threadedly engaged proximal connector assembly 36 and distal connector assembly 38. The exploded view of FIG. 12 depicts the detachment of the guide tube 12 from the secure interim assembly 120 after the introducer assembly 10 has been moved to the introduced mode. The detachment and removal of the tube guide 12 moves the introducer assembly 10 from the introduced mode to the separated mode and a disposable guide tube 12 may be discarded. The exemplary embodiment depicted involves an elongate member 16 (in this embodiment a fiber optic 42) having its length disposed entirely within the secure interim assembly 120.

Figure 13:
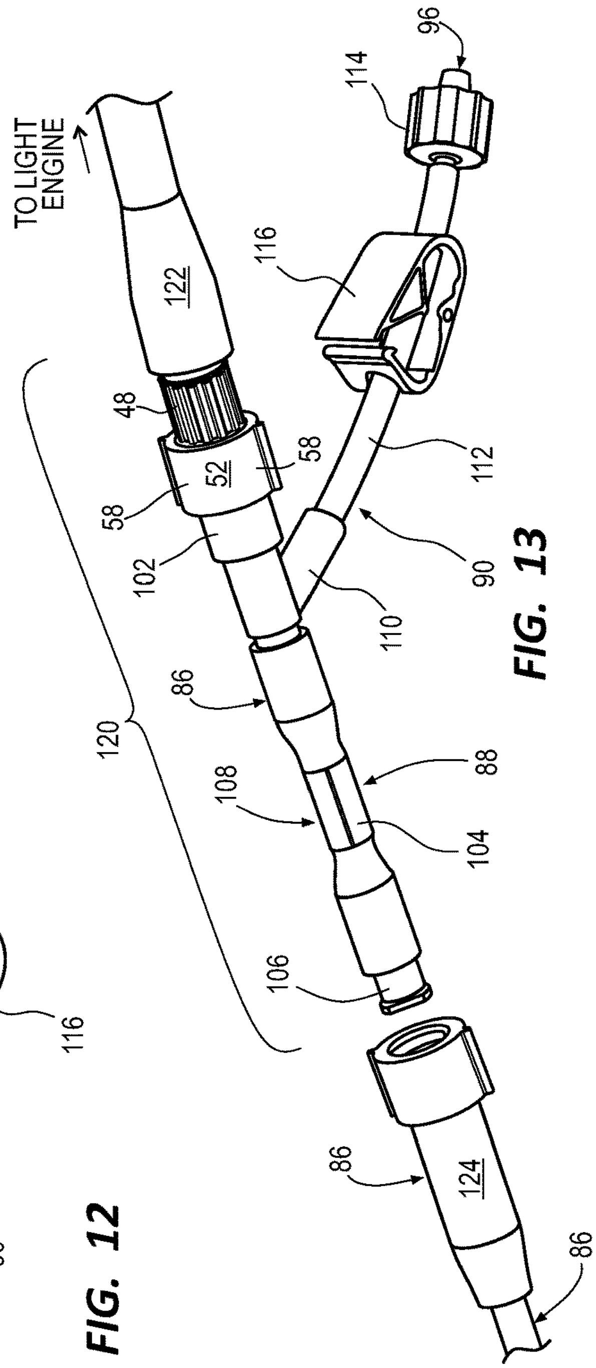
FIG. 13 is a perspective partial exploded view of the exemplary secure interim assembly of FIG. 12 showing the secure interim assembly connected to an optical connector and exploded from connection to an extension set.

FIG. 13 is a perspective view of the exemplary secure interim assembly 120 of FIG. 12 showing that the 3-port adapter 84 is connectable via the threadedly engaged proximal connector assembly 36 and distal connector assembly 38 to a tubular-receiving structure 86 (an optical connector 122 is shown that may be connected via light transmission cable (shown as extending from the optical connector 122) to a light engine (not shown)) to supply light to the fiber optic 42, such light to be emitted to disinfect the 3-port adapter 84 and/or fluids passing through the 3-port adapter 84. FIG. 13 also shows that the 3-port adapter 84 is connectable at its exit port 94 to another tubular-receiving structure 86 (e.g., tubing, an extension set, a catheter, and the like), such that any fluids passing through the side port 96 into or out of the 3-port adapter 84 also pass through, into or out of, the tubular-receiving structure 86. The flow of any such fluids (e.g., fresh dialysate or waste dialysate) may be controlled by clamping or releasing pinch clamp 116.

FIG. 14 is a partially exploded perspective view showing the secure interim assembly 120 connected to an exemplary tubular-receiving structure 86; namely, an extension set 124, with the proximal connector assembly 36 (comprising an SMA fiber connector 44) disconnected and slightly withdrawn to reveal a portion of the fiber optic 42 otherwise partially enclosed within and extending beyond the extension set 124.

FIG. 15 depicts an exemplary fully assembled combination of the secure interim assembly 120 connected to the catheter extension set 124 (shown in FIG. 14) and attached to a tubular-receiving structure 86; namely, an exemplary catheter 126.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Exemplary embodiments of the present invention are described above. No element, act, or instruction used in this description should be construed as important, necessary, critical, or essential to the invention unless explicitly described as such. Although several exemplary embodiments have been described in detail herein, those skilled in the art will readily appreciate that many modifications are possible in these exemplary embodiments without materially departing from the novel teachings and advantages of this invention. For example, the various embodiments of medically related introducer assemblies and introducer systems, as disclosed, and claimed herein, should not limit the scope of the invention to medical situations. Non-medical situation uses are contemplated are adequately enabled. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under Section 112, 6th paragraph is not intended. Additionally, it is not intended that the scope of patent protection afforded the present invention be defined by reading into any claim a limitation found herein that does not explicitly appear in the claim itself.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. An introducer assembly for introducing an elongate member into a tubular-receiving structure, the introducer assembly being configured to have a ready mode, an introduced mode, and a detached mode, the introducer assembly comprising:

a guide tube having a longitudinal axis, a proximal body, and a distal portion being rotatably connected to the proximal body such that the distal portion rotates about the longitudinal axis of the guide tube, the proximal body having a longitudinal slide slot, the guide tube for housing and securing the elongate member when the introducer assembly is in the ready mode, a slide collar having a grip, a slide post, and a centered capture structure suspended from the slide post, the slide collar being disposed such that the grip is accessed outside the guide tube, the slide post is movably slidable within the slide slot, and the centered capture structure is advanceable as suspended from the slide post and remains centered about the longitudinal axis as the slide post is moved slidably, the introducer assembly being movable from the ready mode to the introduced mode, a proximal connector assembly being detachably captured by the centered capture structure and being connected to the elongate member, thereby movably connecting the elongate member to the slide collar, a distal connector assembly is detachably nested within the distal portion of the guide tube and is connectable to the tubular-receiving structure, and wherein the introducer assembly is disposed in the introduced mode when:

the distal connector assembly is connected to the tubular-receiving structure, the distal connector assembly guides the elongate member through the distal connector assembly into the connected tubular-receiving structure as the elongate member is advanced as the slide collar is advanced toward the distal portion, and the distal connector assembly rotates together with the distal portion to rotatably connect to the distal connector assembly and the proximal connector assembly.

2. The introducer assembly of claim 1 wherein the introducer assembly is moved from the introduced mode to the detached mode when the slide collar of the guide tube is detached from the proximal connector assembly leaving the proximal connector assembly connected to the distal connector assembly and the elongate member disposed within the tubular-receiving structure, the proximal connector assembly is detached from the slide collar of the guide tube when the proximal connector is released from nesting within the centered capture structure and the distal connector assembly is detached from nesting within the distal portion of the guide tube.

3. The introducer assembly of claim 2 wherein the detached guide tube is disposable.

4. The introducer assembly of claim 1 wherein an annular snap-fit joint rotatably connects the proximal body of the guide tube to the distal portion of the guide tube.

5. The introducer assembly of claim 4 wherein the annular snap-fit joint comprises a male annular protrusion with an exterior bead and a female annular recess with a furrow, the exterior bead is disposed within the furrow.

6. The introducer assembly of claim 5 wherein the proximal body further comprises the male annular protrusion and the distal portion further comprises the female annular recess.

7. The introducer assembly of claim 1 wherein the elongate member is a selected from the group of elongate members consisting of a probe, a sensor, a camera, a light source, a guide wire, an endoscope, an angioscope, a hysteroscope, a gastroscope, a flexible telescope for colonoscopy, a bronchoscope, a cystoscope, a probe for illumination, a probe for pinpoint medication or treatment delivery, a probe for inflation gas delivery, and a fiber optic.

8. The introducer assembly of claim 1 wherein the elongate member is a fiber optic, and the proximal connector assembly comprises a Subminiature A (SMA) fiber connector and a ferrous ring, the fiber optic connecting to the SMA fiber connector.

9. The introducer assembly of claim 1 wherein the tubular-receiving structure is selected from a group of tubular-receiving structures consisting of an adapter, an extension set, a catheter, and tubing.

10. The introducer assembly of claim 1 wherein the tubular-receiving structure is an adapter, and the adapter comprises a main line, an entry port, an exit port, a branching line, and a side port, the main line is tubular and has the entry port and the exit port disposed at opposite ends of the main line, the branching line communicates with the main line and has the side port.

11. An introducer system for introducing an elongate member into a tubular-receiving structure, the introducer system comprises:

an adapter and an introducer assembly being configured to have a ready mode, an introduced mode, and a detached mode, the introducer assembly comprising:

a guide tube having a longitudinal axis, a proximal body, and a distal portion being rotatably connected to the proximal body such that the distal portion rotates about the longitudinal axis of the guide tube, the proximal body having a longitudinal slide slot, the guide tube for housing and securing the elongate member when the introducer assembly is in the ready mode, a slide collar having a grip, a slide post, and a centered capture structure suspended from the slide post, the slide collar being disposed such that the grip is accessed outside the guide tube, the slide post is movably slidable within the slide slot, and the centered capture structure is advanceable as suspended from the slide post and remains centered about the longitudinal axis as the slide post is moved slidably, the introducer assembly being movable from the ready mode to the introduced mode, a proximal connector assembly being detachably captured by the centered capture structure and being connected to the elongate member, thereby movably connecting the elongate member to the slide collar, a distal connector assembly is detachably nested within the distal portion of the guide tube and is connectable to the tubular-receiving structure, and wherein the introducer assembly is disposed in the introduced mode when:

the distal connector assembly is connected to the adapter, the adapter is connected to the tubular-receiving structure and disposed intermediate of the distal connector assembly and the tubular-receiving structure, the distal connector assembly guides the elongate member through the distal connector assembly into the adapter as the elongate member is advanced as the slide collar is advanced toward the distal portion, and the distal connector assembly rotates together with the distal portion to rotatably connect to the distal connector assembly and the proximal connector assembly.

12. The introducer system of claim 11 wherein the introducer assembly is moved from the introduced mode to the detached mode when the slide collar of the guide tube is detached from the proximal connector assembly leaving the proximal connector assembly connected to the distal connector assembly and the elongate member disposed within the adapter, the proximal connector assembly is detached from the slide collar of the guide tube when the proximal connector is released from nesting within the centered capture structure and the distal connector assembly is detached from nesting within the distal portion of the guide tube.

13. The introducer system of claim 12 wherein the detached guide tube is disposable.

14. The introducer system of claim 11 wherein an annular snap-fit joint rotatably connects the proximal body of the guide tube to the distal portion of the guide tube.

15. The introducer system of claim 14 wherein the annular snap-fit joint comprises a male annular protrusion with an exterior bead and a female annular recess with a furrow, the exterior bead is disposed within the furrow.

16. The introducer system of claim 15 wherein the proximal body further comprises the male annular protrusion and the distal portion further comprises the female annular recess.

17. The introducer system of claim 11 wherein the adapter comprises a main line, an entry port, an exit port, a branching line, and a side port, the main line is tubular and has the entry port and the exit port disposed at opposite ends of the main line, the branching line communicates with the main line and has the side port.

18. The introducer system of claim 17 wherein the entry port is connected to the distal connector assembly, the exit port is connected to the tubular-receiving structure, the side port is connected to a second tubular-receiving structure, the elongate member passes through the entry port into the main line of the adapter as the elongate member is advanced as the slide collar is advanced toward the distal portion.

19. The introducer system of claim 18 wherein the adapter is configured to allow uninhibited flow of a fluid through the exit port, the main line, the branching line, the side port, and into and out of the second tubular-receiving structure.

20. An introducer assembly for introducing a fiber optic into a tubular-receiving structure, the introducer assembly being configured to have a ready mode, an introduced mode, and a detached mode, the introducer assembly comprising:

a guide tube having a longitudinal axis, a proximal body, and a distal portion being rotatably connected to the proximal body such that the distal portion rotates about the longitudinal axis of the guide tube, the proximal body having a longitudinal slide slot, the guide tube for housing and securing the elongate member when the introducer assembly is in the ready mode, a slide collar having a grip, a slide post, and a centered annular cylinder suspended from the slide post, the slide collar being disposed such that the grip is accessed outside the guide tube, the slide post is movably slidable within the slide slot, and the centered annular cylinder is advanceable as suspended from the slide post and remains centered about the longitudinal axis as the slide post is moved slidably, the introducer assembly being movable from the ready mode to the introduced mode, a proximal connector assembly comprising a Subminiature A (SMA) fiber connector and a ferrous ring, the proximal connector assembly being detachably captured by the centered annular cylinder and the SMA fiber connector being connected to the fiber optic, thereby movably connecting the fiber optic to the slide collar, a distal connector assembly comprising a distal luer and a luer attachment ring, the distal connector assembly is detachably nested within the distal portion of the guide tube and the distal luer is connectable to the tubular-receiving structure, and wherein the introducer assembly is disposed in the introduced mode when:

the distal luer is connected to the tubular-receiving structure, the distal luer has a longitudinal passageway through which the fiber optic is guided into the connected tubular-receiving structure as the fiber optic is advanced by advancing movement of the slide collar toward the distal portion, and the distal connector assembly rotates together with the distal portion to rotatably connect the distal connector assembly to the proximal connector assembly.

* * * * *